US006989381B2

(12) United States Patent
Sims

(10) Patent No.: US 6,989,381 B2
(45) Date of Patent: *Jan. 24, 2006

(54) SOLUTION COMPOSITION OF AN OXAZOLIDINONE ANTIBIOTIC DRUG HAVING ENHANCED DRUG LOADING

(75) Inventor: Sandra M. Sims, Portage, MI (US)

(73) Assignee: Pharmacia Corporation, St. Louis, MO (US)

( * ) Notice: Subject to any disclaimer, the term of this patent is extended or adjusted under 35 U.S.C. 154(b) by 320 days.

This patent is subject to a terminal disclaimer.

(21) Appl. No.: 09/933,366

(22) Filed: Aug. 20, 2001

(65) Prior Publication Data

US 2002/0068720 A1 Jun. 6, 2002

Related U.S. Application Data

(60) Provisional application No. 60/285,347, filed on Apr. 10, 2001, provisional application No. 60/226,846, filed on Aug. 22, 2000.

(51) Int. Cl.
A61K 31/535 (2006.01)
(52) U.S. Cl. ................................. 514/235.5; 514/236.8
(58) Field of Classification Search ............. 514/235.5, 514/236.8
See application file for complete search history.

(56) References Cited

U.S. PATENT DOCUMENTS

| 4,524,068 | A | 6/1985 | Szejtli et al. ................ 514/58 |
| 4,599,327 | A | 7/1986 | Nógrádi et al. .............. 514/58 |
| 4,727,064 | A | 2/1988 | Pitha .......................... 514/58 |
| 5,024,998 | A | 6/1991 | Boder ......................... 514/58 |
| 5,134,127 | A | 7/1992 | Stella et al. .................. 514/58 |
| 5,164,510 | A | 11/1992 | Brickner .................... 548/231 |
| 5,231,188 | A | 7/1993 | Brickner .................... 548/221 |
| 5,324,718 | A | 6/1994 | Loftsson ...................... 514/58 |
| 5,376,645 | A | 12/1994 | Stella et al. .................. 514/58 |
| 5,486,508 | A | 1/1996 | Uda et al. .................... 514/58 |
| 5,538,721 | A | 7/1996 | Babcock et al. .......... 424/78.04 |
| 5,565,571 | A | 10/1996 | Barbachyn et al. ......... 546/144 |
| 5,627,181 | A | 5/1997 | Riedl et al. .............. 514/236.8 |
| 5,646,294 | A * | 7/1997 | Bartroli et al. ............ 548/267.2 |
| 5,652,238 | A | 7/1997 | Brickner et al. ......... 514/235.8 |
| 5,670,530 | A | 9/1997 | Chen et al. ................ 514/366 |
| 5,688,792 | A * | 11/1997 | Barbachyn et al. ...... 514/235.5 |
| 5,698,574 | A | 12/1997 | Riedl et al. ................ 514/376 |
| 5,756,546 | A | 5/1998 | Pirotte et al. .............. 514/605 |
| 5,807,895 | A | 9/1998 | Stratton et al. ............. 514/573 |
| 5,824,668 | A | 10/1998 | Rubinfeld et al. .......... 514/170 |
| 5,837,870 | A | 11/1998 | Pearlman et al. ........... 544/137 |
| 5,874,418 | A | 2/1999 | Stella et al. .................. 514/58 |
| 5,910,504 | A | 6/1999 | Hutchinson ................ 514/376 |
| 6,046,177 | A | 4/2000 | Stella et al. .................. 514/58 |
| 6,069,145 | A | 5/2000 | Betts .......................... 514/252 |
| 6,133,248 | A | 10/2000 | Stella .......................... 514/58 |
| 6,284,747 | B1 | 9/2001 | Rubinfeld .................... 514/58 |
| 6,316,020 | B1 | 11/2001 | Whittle et al. ............. 424/439 |
| 6,337,329 | B1 | 1/2002 | Cochran et al. ......... 514/235.8 |
| 6,407,079 | B1 | 6/2002 | Müller et al. ................ 514/58 |
| 2002/0156072 | A1 | 10/2002 | Barbachyn et al. ...... 514/227.8 |

FOREIGN PATENT DOCUMENTS

| EP | 0 340 171 | 11/1989 |
| WO | WO 85/02767 | 7/1985 |
| WO | WO 96/32135 | 10/1996 |
| WO | WO 96/38175 | 12/1996 |
| WO | WO 97/36935 | 10/1997 |
| WO | WO 97/39770 | 10/1997 |
| WO | WO 98/37884 | 9/1998 |
| WO | WO 98/55148 | 12/1998 |
| WO | WO 98/58677 | 12/1998 |
| WO | WO 99/24073 | 5/1999 |
| WO | WO 99/24393 | 5/1999 |
| WO | WO 99/27932 | 6/1999 |
| WO | WO00/18387 | 4/2000 |
| WO | WO01/19366 | 3/2001 |
| WO | WO02/30395 | 4/2002 |

OTHER PUBLICATIONS

Bekers et al. Drug Development and Industrial Pharmacy. 17, 1503-1549. (1991).
Loftsson. Pharmazie. 53, 733-740. (1998).
Rajewski. Pharmaceutical Applications of Cyclodextrins. In Journal of Pharmaceutical Sciences. 85(11), pp. 1154-1159. (1996).
Szejtli Cyclodextrins and Their Inclusion Complexes. Chinoin Research Center, Hungary. pp. 204-232. (1982).
Szejtli. Medical Research Reviews. 14, 353-386. (1994).
Zhang et al. Expert Opinion on Therapeutic Patents. 9, 1697-1717. (1999).

(Continued)

Primary Examiner—Christopher S. F. Low
Assistant Examiner—C. Delacroix-Muirheid
(74) Attorney, Agent, or Firm—Charles W. Ashbrook; Karen B. King

(57) ABSTRACT

There is provided a pharmaceutical composition for therapeutic or prophylactic administration to a subject having an infective disease or condition or at risk thereof. The composition comprises an aqueous carrier having in solution therein (a) an oxazolidinone antimicrobial drug, for example linezolid, in a therapeutically or prophylactically effective drug concentration that is above the practical limit of solubility of the drug in a substantially isotonic aqueous solution at a physiologically compatible pH, and (b) a pharmaceutically acceptable cyclodextrin compound in a concentration sufficient to maintain the drug in solution at such a drug concentration. The composition is particularly useful for intravenous delivery of the drug.

30 Claims, 1 Drawing Sheet

OTHER PUBLICATIONS

Arima et al., (2001), Comparative Studies of the Enhancing Effects of Cyclodextrins on the Solubility and Oral Bioavailibility of Tacrolimus in Rats, *Journal of Pharmaceutical Sciences*, vol. 90, No. 6, pp. 690-701.

Conners, (1997), The Stability of Cyclodextrin Complexes in Solution, *Chem. Rev.* 97, pp. 1325-1357.

Faucci et al., (2002), Computer-aided molecular modeling techniques for predicting the stability of drug-cyclodextrin inclusion complexes in aqueous solutions, 358, pp. 383-390.

Lipkowitz, (1998), Applications of Computational Chemistry to the Study of Cyclodextrins, *Chem. Rev.*, 98, ppo. 1829-1873.

Lotsson et al., (1989), Effects of 2-hydroxpropyl-β-cyclodextrin on the aqueous solubility of drugs and transdermal delivery of 17β-estradiol, *Acta Pharm. Nord.*, 1(4), pp. 185-194.

Loftsson, et al., (1991), Solubilization and stabilization of drugs through cyclodextrin complexation, *Act Pharm. Nord.*, 3(4), pp. 215-217.

Loftsson et al., (1996), Pharmaceutical Applications of Cyclodextrins. 1. Drug Soulubilization and Stabilization, *Journal of Pharmaceutical Sciences*, vol. 85, No. 10, pp. 1017-1025.

Pagington, (1987), β-Cyclodextrin: the success of molecular inclusion, *Chemistry in Britain*, pp. 455-458.

Pitha et al., (1983), Molecular Encapsulation of Drugs By Cyclodextrins And Congeners, *Controlled Drug Delivery*, vol. 1, pp. 125-148.

Pitha et al., (1986), Hydroxypropyl-β-cyclodextrin: preparation and characterization; effects on solubility of drugs, *International Journal of Pharmaceutics*, 29, pp. 73-82.

Schneider et al., (1998), NMR Studies of Cyclodextrins and Cyclodextrin Complexes, *Chem. Rev.*, 98, pp. 1755-1785.

Stella, (1997), Cyclodextrins: Their Future in Drug Formulation and Delivery, *Pharmaceutical Research*, vol. 14, No. 5, pp. 556-567.

Szejtli, (1998), Introduction and General Overview of Cyclodextrin Chemistry, *Chem. Rev.*, 98, pp. 1743-1753.

Uekama, (1987), Cyclodextrin Inclusion Compounds: Effects on Stability and Bio-Pharmaceutical Properties, *Topics in Pharmaceutical Sciences*, pp. 181-194.

Uekama et al., (1987), Cyclodextrins in Drug Carrier Systems, *Critical Reviews in Therapeutic Drug Carrier Systems*, 3(1), pp. 1-40.

Uekama et al., (1998), Cyclodextrin Drug Carrier System, *Chem. Rev.*, 98, pp. 2045-2076.

Hilliard, (1999), The Complexation of Hydroxypropyl-β-Cyclodextrin with Oxazolidinones: A Study on the Effect of Cyclodextrins in Terms of Solubility Enhancement, Increased Dissolution Rate, and Precipitation Inhibition.

* cited by examiner

SOLUTION COMPOSITION OF AN OXAZOLIDINONE ANTIBIOTIC DRUG HAVING ENHANCED DRUG LOADING

This application claims the benefit of U.S. Provisional Application No. 60/285,347, filed Apr. 10, 2001 and of U.S. Provisional Application No. 60/226,846, filed Aug. 22, 2000.

FIELD OF THE INVENTION

The present invention relates to a pharmaceutical composition in aqueous solution form useful for oral, parenteral or topical application to a subject for treatment or prevention of infective disease. In particular, the present invention relates to such a composition having as an active agent an oxazolidinone antibiotic drug. The field of the present invention also includes therapeutic or prophylactic use of such a composition, and use of such a composition in preparation of a medicament.

BACKGROUND OF THE INVENTION

Numerous oxazolidinone compounds have been reported having therapeutically and/or prophylactically useful antibiotic or antimicrobial, in particular antibacterial, effect. Among such compounds are those illustratively disclosed in the following patents, each of which is individually incorporated herein by reference.

U.S. Pat. No. 5,164,510 to Brickner.
U.S. Pat. No. 5,231,188 to Brickner.
U.S. Pat. No. 5,565,571 to Barbachyn & Brickner.
U.S. Pat. No. 5,627,181 to Riedl et al.
U.S. Pat. No. 5,652,238 to Barbachyn et al.
U.S. Pat. No. 5,688,792 to Barbachyn et al.
U.S. Pat. No. 5,698,574 to Riedl et al.
U.S. Pat. No. 6,069,145 to Betts.

Compounds disclosed in above-cited U.S. Pat. No. 5,688,792 include for example the compound (S)-N-[[3-[3-fluoro-4-(4-morpholinyl)phenyl]-2-oxo-5-oxazolidinyl]methyl]acetamide, also referred to herein as linezolid. Linezolid has the structure shown in formula (I):

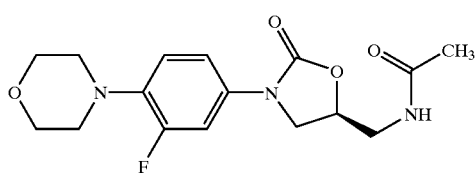

(I)

and is in commercial use as a medicament under the trademark Zyvox® of Pharmacia Corporation. Linezolid exhibits strong antibacterial activity against gram-positive organisms including those of the following genera: *Staphylococcus* (e.g., *Staphylococcus aureus, Staphylococcus epidermis*), *Streptococcus* (e.g., *Streptococcus viridans, Streptococcus pneumoniae*), *Enterococcus* (e.g., *Enterococcus fecalis, Enterococcus faecium*), *Bacillus, Corynebacterium, Chlamydia* and *Neisseria*. Many such gram-positive organisms have developed significant levels of resistance to other antibiotics. Oxazolidinone antibiotics are also generally effective against anaerobic organisms such as those of the genera *Bacteroides* and *Clostridia*, and against acid-fast organisms such as those of the genus *Mycobacterium*.

Above-cited U.S. Pat. No. 5,688,792 discloses that the subject antibiotic oxazolidinone compounds, including linezolid, can be formulated as liquid form compositions including solutions. For example, it is disclosed therein that a solution can be provided of a subject oxazolidinone compound in water or in a water-propylene glycol or water-polyethylene glycol system, optionally containing conventional coloring agents, flavoring agents, stabilizers and thickening agents.

It is further disclosed in above-cited U.S. Pat. No. 5,688,792 that the subject oxazolidinone compounds can be administered orally, parenterally and/or topically, and that parenteral administration can be by intravenous injection or other parenteral route. For parenteral administration, it is disclosed therein that a suitable composition will generally contain a pharmaceutically acceptable amount of a subject oxazolidinone compound as a soluble salt dissolved in a liquid carrier such as water for injection to form a suitably buffered isotonic solution. Such a solution is stated therein generally to contain a subject oxazolidinone compound dissolved in the carrier in an amount sufficient to provide an injectable concentration of about 1 to about 400 mg/ml of solution.

Many oxazolidinone compounds useful as antibiotics do not form, or do not readily form, salts. For these compounds, and where for any reason it is preferred not to provide the antibiotic in salt form, it is generally difficult to formulate the antibiotic as a solution in a pharmaceutically acceptable liquid carrier, particularly an aqueous carrier. Most such compounds have relatively low solubility in water; in the case of linezolid, for example, the solubility at ambient temperature is less than 3 mg/ml and the practical limit of concentration in aqueous solution is about 2 mg/ml.

Particularly where parenteral or oral administration of an oxazolidinone antibiotic drug is contemplated, it is desired to achieve systemic concentrations of the drug in the bloodstream above a minimum inhibitory concentration for 90% of target organisms ($MIC_{90}$). It will readily be understood that it is difficult to achieve such concentrations by administration of a relatively small volume of a composition wherein the drug is present in dissolved form, unless the composition has a relatively high drug loading, and in particular a drug loading substantially above the limit of solubility in water of most oxazolidinone antibiotics not in the form of a salt.

A need therefore exists for a solution composition of an oxazolidinone antibiotic drug having a drug loading substantially in excess of the practical limit of solubility of the drug in water. A particular need exists for a parenterally deliverable solution composition of an oxazolidinone antibiotic drug having a relatively high concentration of the drug.

These and other needs will be seen to be met by the invention now described.

SUMMARY OF THE INVENTION

The present invention provides a pharmaceutical composition suitable for therapeutic or prophylactic administration to a subject having or at risk of infective disease, the composition comprising an aqueous carrier having in solution therein (a) an oxazolidinone antimicrobial drug in a therapeutically or prophylactically effective drug concentration that is above the practical limit of solubility of the drug in a substantially isotonic aqueous solution at a physiologically compatible pH, e.g., pH 4.8, and (b) a pharmaceutically acceptable cyclodextrin compound in a concentration sufficient to maintain the drug in solution at such a drug concentration. Preferably the drug concentration is in a range of about 3 to about 100 mg/ml.

The term "suitable for therapeutic or prophylactic administration" in the present context encompasses compositions that are suitable for direct administration as formulated, and also compositions that are suitable for administration upon dilution in an appropriate pharmaceutically acceptable liquid. Where the composition is intended for direct administration as formulated, the drug concentration is more preferably about 4 to about 40 mg/ml and most preferably about 5 to about 10 mg/ml. Where the composition is intended for dilution prior to administration, the drug concentration is more preferably about 10 to about 100 mg/ml and most preferably about 30 to about 100 mg/ml.

It is believed, without being bound by theory, that the enhanced solubility of the drug in a composition of the invention is due to association of at least a portion of the drug with the cyclodextrin. It is further believed that at least one mechanism by which the drug associates with the cyclodextrin compound to enhance solubility of the drug in an aqueous medium is through formation of an inclusion complex. Such complexes or conjugates are known in the art to form with a variety of drugs, and a number of advantages have been postulated for use of cyclodextrin-drug complexes in pharmacy. See for example review articles by Bekers et al. (1991) in *Drug Development and Industrial Pharmacy*, 17, 1503–1549; Szejtli (1994) in *Medical Research Reviews*, 14, 353–386; and Zhang & Rees (1999) in *Expert Opinion on Therapeutic Patents*, 9, 1697–1717.

Formulations of various drugs with various cyclodextrins have been proposed in the patent literature, including the patents and publications referenced below.

U.S. Pat. No. 5,670,530 to Chen & Shishido discloses compositions comprising a rhodacyanine anti-cancer agent and a cyclodextrin.

U.S. Pat. No. 5,756,546 to Pirotte et al. discloses compositions comprising nimesulide and a cyclodextrin.

U.S. Pat. No. 5,807,895 to Stratton et al. discloses compositions comprising a prostaglandin and a cyclodextrin.

U.S. Pat. No. 5,824,668 to Rubinfeld et al. discloses compositions comprising a 5β steroid drug and a cyclodextrin.

International Patent Publication No. WO 96/32135 discloses compositions comprising propofol and a cyclodextrin.

International Patent Publication No. WO 96/38175 discloses compositions comprising an antiulcerative benzimidazole compound and a branched cyclodextrin-carboxylic acid.

International Patent Publication No. WO 97/39770 discloses compositions comprising a thrombin inhibitor and a cyclodextrin.

International Patent Publication No. WO 98/37884 discloses compositions comprising a 3,4-diarylchroman compound and a cyclodextrin.

International Patent Publication No. WO 98/55148 discloses compositions comprising a sparingly water-soluble drug, a cyclodextrin, a water-soluble acid and a water-soluble organic polymer.

International Patent Publication No. WO 98/58677 discloses compositions comprising voriconazole and a cyclodextrin.

International Patent Publication No. WO 99/24073 discloses compositions comprising a taxoid such as paclitaxel or docetaxel and a cyclodextrin.

International Patent Publication No. WO 99/27932 discloses compositions comprising an antifungal compound of defined formula and a cyclodextrin.

However, the degree of enhancement of solubility achievable through complexation with cyclodextrins of a particular drug or class of drugs is not generally predictable. Cyclodextrins are expensive excipients and in many cases the degree of enhancement of solubility, or other benefit obtained, has not economically justified the increased cost of a formulation arising from addition of a cyclodextrin. The present invention is based in part on the discovery that addition of a relatively modest amount of a cyclodextrin compound increases the solubility of an oxazolidinone antibiotic drug to a surprising degree. This enhancement in solubility, among other benefits, makes it possible for the first time to deliver intravenously a therapeutically or prophylactically effective dose of the oxazolidinone in a volume small enough to be clinically acceptable and convenient, even for subjects intolerant of large volume intravenous infusion because of hypertension, cardiac, renal and/or other problems. For example, a 600 mg dose of linezolid can, through use of a composition of the present invention, be delivered intravenously in a volume of 100 ml or less.

The term "pharmaceutically acceptable" in relation to a cyclodextrin or other excipient herein means having no persistent detrimental effect on the health of the subject being treated. The pharmaceutical acceptability of a cyclodextrin depends, among other factors, on the particular cyclodextrin compound in question, on its concentration in the administered composition, and on the route of administration. For example, use of β-cyclodextrin as an excipient in intravenous compositions is limited by hemolytic and nephrotoxic effects, but is generally non-toxic when administered orally.

The term "practical limit of solubility" in relation to a drug means the highest concentration at which the drug can be formulated in solution without risk of precipitation or crystallization of the drug during the normal range of manufacturing, packaging, storage, handling and use conditions. Typically the practical limit of solubility is considerably lower than the true solubility limit in a given aqueous medium, for example about 70% of the true solubility limit. Thus, illustratively, for a drug having a true solubility limit in a given aqueous medium of 2.9 mg/ml, the practical limit of solubility is likely to be about 2 mg/ml.

Except where the context demands otherwise, use of the singular herein will be understood to embrace the plural. For example, by indicating above that a composition of the invention comprises "an oxazolidinone antibiotic drug" and "a pharmaceutically acceptable cyclodextrin compound", it will be understood that the composition can contain one or more such drugs and one or more such cyclodextrin compounds.

The invention also provides a method of preparing a medicament for treating or preventing infective disease, using a composition as described above.

Also embraced by the present invention is a method of treating or preventing infective disease in a subject, the method comprising administration to the subject of a composition as described above in a therapeutically or prophylactically effective dose. Such administration can be oral, parenteral or topical, but is preferably parenteral and more preferably by intravenous injection or infusion.

The method of the invention is particularly useful where the infective disease arises through infection by one or more gram-positive bacteria, for example those of the genera *Staphylococcus* (e.g., *Staphylococcus aureus*, *Staphylococ-* cus epidermidis), Streptococcus (e.g., Streptococcus viridans, Streptococcus pneumoniae), Enterococcus (e.g., Enterococcus fecalis, Enterococcus faecium), Bacillus, Corynebacterium, Chlamydia and Neisseria; anaerobic organisms, for example those of the genera Bacteroides and Clostridia; and acid-fast organisms, for example those of the genus Mycobacterium. The method of the invention is especially useful where infection is by a strain of gram-positive bacteria that is resistant to one or more non-oxazolidinone antibiotics.

DETAILED DESCRIPTION OF THE INVENTION

Figure 1:
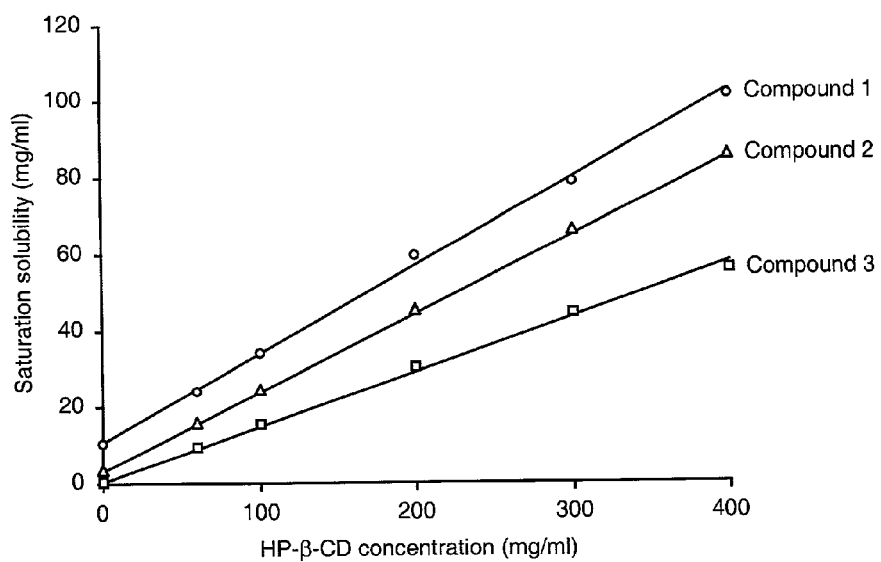
FIG. 1 is a graphical representation of data from the study described in Example 6 herein, and demonstrates enhanced saturation solubility of oxazolidinone compounds in aqueous solutions containing hydroxypropyl-β-cyclodextrin (HP-β-CD).

Any oxazolidinone antimicrobial drug, i.e., one having an oxazolidinone moiety as part of its chemical structure, can be formulated with a cyclodextrin compound in accordance with the invention. Preferred oxazolidinones are compounds having formula (II):

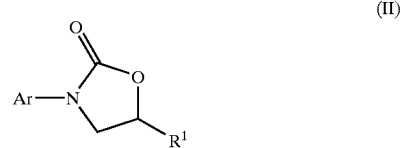

where Ar is an optionally substituted aryl or heteroaryl group and $R^1$ is a group selected such that the compound of formula (II) falls within the scope of compounds generically or specifically disclosed in any of the following patents, each of which is individually incorporated herein by reference.

U.S. Pat. No. 5,164,510 to Brickner.
U.S. Pat. No. 5,231,188 to Brickner.
U.S. Pat. No. 5,565,571 to Barbachyn & Brickner.
U.S. Pat. No. 5,627,181 to Riedl et al.
U.S. Pat. No. 5,652,238 to Barbachyn et al.
U.S. Pat. No. 5,688,792 to Barbachyn et al.
U.S. Pat. No. 5,698,574 to Riedl et al.
U.S. Pat. No. 6,069,145 to Betts.

More preferably Ar is an optionally substituted 5- or 6-membered aryl or heteroaryl ring having 0 to 3 heteroatoms selected from nitrogen, oxygen and sulfur.

Still more preferably Ar is a group

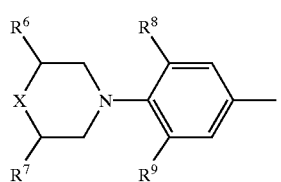

where X is O, S, SO, $SO_2$, $SNR^4$, $S(O)NR^4$, $NR^4$ or $NC(O)CH_2OR^4$, where $R^4$ is selected from hydrogen, $R^5$ and $—C(O)R^5$ groups where $R^5$ is $C_{1-8}$hydrocarbyl optionally substituted with one or more hydroxy, fluorine or chlorine groups; $R^6$ and $R^7$ are independently selected from hydrogen, methyl and cyano groups; and $R^8$ and $R^9$ are independently selected from hydrogen, fluorine and chlorine atoms. Most preferably $R^6$ and $R^7$ are hydrogen, and one of $R^8$ and $R^9$ is fluorine and the other of $R^8$ and $R^9$ is hydrogen.

Preferably $R^1$ is a group $—(CH_2)_nN(R^2)COR^3$ where n is 1 to 3, and $R^2$ and $R^3$ are independently selected from hydrogen and $C_{1-8}$hydrocarbyl optionally substituted with one or more hydroxy, fluorine or chlorine groups.

Examples of preferred oxazolidinones are compounds selected from linezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide, (S)-N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide. In one especially preferred embodiment, the oxazolidinone is linezolid. In another especially preferred embodiment, the oxazolidinone is N-[[(5S)-3-[4-(1,1-dioxido-4-thiomorpholinyl)-3,5-difluorophenyl]-2-oxo-5-oxazolidinyl]methyl]acetamide.

The invention is illustrated herein with particular reference to linezolid, and it will be understood that any other oxazolidinone antimicrobial drug can, if desired, be substituted in whole or in part for linezolid, with appropriate adjustment in concentration and dosage ranges, in the compositions and methods herein described.

Oxazolidinone compounds used in compositions of the invention can be prepared by a process known per se, in the case of linezolid, for example, by processes described in the following patents, each of which is individually incorporated herein by reference.

Above-cited U.S. Pat. No. 5,688,792.
U.S. Pat. No. 5,837,870 to Barbachyn et al.
International Patent Publication No. WO 99/24393.

Other oxazolidinone compounds can be prepared by processes known per se, including processes set forth in patent publications disclosing such drugs.

Linezolid is usefully present in a composition of the invention at a concentration of about 3 mg/ml to as high a concentration as is practically enabled by the cyclodextrin present therewith, for example about 100 mg/ml. Preferably in a composition intended for direct administration as formulated, the concentration of linezolid is about 4 to about 40 mg/ml, more preferably about 5 to about 10 mg/ml, for example about 6 mg/ml. Preferably in a composition intended for dilution in a pharmaceutically acceptable liquid prior to administration, the concentration of linezolid is about 10 to about 100 mg/ml, more preferably about 30 to about 100 mg/ml, for example about 60 mg/ml. Useful concentrations of other oxazolidinone drugs are those that are therapeutically equivalent to the linezolid concentration ranges given immediately above.

The cyclodextrin compound with which the oxazolidinone antibiotic drug is formulated according to the present invention is preferably selected from (α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxyalkylcyclodextrins (e.g., carboxymethyl-β-cyclodextrin) and sulfoalkylether cyclodextrins (e.g., sulfobutylether-β-cyclodextrin). More preferred are hydroxyalkyl-β-cyclodextrins and sulfoalkylether-β-cyclodextrins; still more preferred are hydroxypropyl-β-cyclodextrin and sulfobutylether-β-cyclodextrin, with sulfobutylether-β-cyclodextrin being presently the most preferred.

If desired, complexation of an oxazolidinone antibiotic drug by a cyclodextrin can be increased by addition of a water-soluble polymer such as carboxymethylcellulose or a salt thereof, hydroxypropylmethylcellulose or polyvinylpyrrolidone, as described by Loftsson (1998), *Pharmazie*, 53, 733–740.

The cyclodextrin is present at a concentration effective to enhance the solubility of the oxazolidinone, for example at a concentration of about 1 to about 500 mg/ml. In practice and in view of the high cost of cyclodextrins, the amount of the cyclodextrin present in a composition of the invention is preferably only slightly greater, for example no more than about 50% greater, than a minimum amount required to maintain the oxazolidinone in solution at the desired oxazolidinone concentration.

Typically, where the composition is intended for direct administration as formulated, suitable concentrations of cyclodextrin will be found in a range from about 5 to about 200 mg/ml, more commonly about 10 to about 100 mg/ml, and most commonly about 20 to about 80 mg/ml. Where the composition is intended for dilution prior to administration, the concentration of cyclodextrin can be significantly higher, for example about 100 to about 500 mg/ml.

One or more pharmaceutically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, citrate/phosphate, sodium bicarbonate and ammonium chloride. Such acids, bases and buffers are included in an amount required to maintain pH of the composition in a physiologically acceptable range, particularly where the composition is intended for parenteral delivery.

One or more pharmaceutically acceptable salts or other solutes can be included in the composition in an amount required to bring osmolality of the composition into a physiologically acceptable range, particularly where the composition is intended for parenteral delivery. Such salts include those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate, with sodium chloride being especially preferred. Other solutes suitable for adjustment of osmolality include sugars, for example dextrose.

Accordingly, a particular embodiment of the invention is a composition as described hereinabove, further comprising a buffering agent and/or an agent for adjusting osmolality in amounts whereby the solution is substantially isotonic and has a physiologically acceptable pH.

Other pharmaceutically acceptable excipients can also be included as desired in compositions of the invention, having functions conventional in the art and in amounts consistent with those functions. For example, a water-soluble organic solvent can be included if desired, as disclosed in U.S. Pat. No. 5,486,508 to Nishida et al., which contemplates a composition suitable for injection comprising a slightly water-soluble drug, a cyclodextrin and a water-soluble organic solvent.

Compositions of the present invention can be prepared by processes known in the art, including by simple admixture, with agitation as appropriate, of the ingredients. Preferably an aqueous solution of the cyclodextrin compound is first prepared, and the oxazolidinone in finely divided solid particulate form is added to that solution with agitation until it is fully dissolved. Where it is desired to prepare a buffered isotonic solution, for example for intravenous infusion, buffering agents and agents for adjustment of osmolality can be added at any stage but are preferably present in solution with the cyclodextrin compound before addition of the oxazolidinone. Processes for preparing a composition of the invention, particularly one intended for parenteral use, are preferably conducted so as to provide a sterile product.

Compositions of the invention intended for parenteral administration are generally suitable for packaging and dispensing in conventional intravenous delivery bags and apparatus.

A contemplated composition can be dried, for example by spray drying, to form a reconstitutable powder. The powder can be dissolved in sterile water to reconstitute a parenterally deliverable composition as herein described.

In a method of the invention for treating or preventing infective disease, a composition as described above in a therapeutically or prophylactically effective daily dose is administered to a subject in need thereof. Such administration can be oral, parenteral or topical, but is preferably parenteral and more preferably by intravenous injection or infusion.

In a particular embodiment of the invention, a method for treating or preventing infective disease comprises (a) diluting a composition as described herein in a pharmaceutically acceptable liquid to form a diluted composition suitable for direct administration, and (b) administering the diluted composition in a therapeutically or prophylactically effective daily dose to a subject in need thereof. Preferably such administration is parenteral and the liquid in which the composition is diluted is a parenterally acceptable aqueous carrier, for example saline or a substantially isotonic buffered aqueous solution having a physiologically compatible pH.

As indicated above, a method of the invention is particularly useful where the infective disease arises through infection by one or more gram-positive bacteria. Where broader-spectrum antibacterial activity, extending to gram-negative bacteria, is required, a second antimicrobial drug can be administered in co-therapy, including for example coformulation, with the present composition. The second antimicrobial drug is selected to be effective against target gram-negative bacteria. Such co-therapy and coformulation are embodiments of the present invention.

The second antimicrobial drug can illustratively be selected from aminoglycosides, cephalosporins, diaminopyridines, fluroquinolones, sulfonamides and tetracyclines. Among particular antimicrobial drugs of these and other classes, each of the following may illustratively be useful as the second antimicrobial drug according to an embodiment of the present invention: amikacin, cefixime, cefoperazone, cefotaxime, ceftazidime, ceftizoxime, ceftriaxone, chloramphenicol, ciprofloxacin, clindamycin, colistin, domeclocycline, doxycycline, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim.

The present invention also encompasses therapeutic and prophylactic methods involving administration of an antibacterial composition as described herein in co-therapy, including for example coformulation, with one or more drugs other than antibacterial drugs.

Therapeutic and prophylactic methods of the invention are useful for any subject in need thereof. The subject is preferably warm-blooded, more preferably mammalian, and most preferably human. However, a particular embodiment of the invention is a veterinary method of treating a non-human subject, for example a domestic, farm or zoo animal, having or at risk of infective disease, with a composition of the invention.

An appropriate dosage, frequency and duration of administration, i.e., treatment regimen, to be used in any particular situation will be readily determined by one of skill in the art without undue experimentation, and will depend, among other factors, on the particular oxazolidinone compound(s) present in the composition, on the particular infective disease or condition to be treated or prevented, on the age, weight and general physical condition of the subject, and on other medication being administered to the subject. It is preferred that response to treatment according to the present method be monitored and the treatment regimen be adjusted if necessary in light of such monitoring.

Where the oxazolidinone is linezolid, a daily dose for a human subject will typically be about 100 mg to about 1000 mg, more typically about 250 mg to about 750 mg, for example about 600 mg of linezolid, administered in a composition of the invention. For other oxazolidinones, a daily dose that is therapeutically equivalent to the above dose ranges for linezolid can be administered.

EXAMPLES

The following Examples illustrate aspects of the present invention but are not to be construed as limitations.

Example 1

A study was conducted to examine solubility of linezolid in an aqueous system containing sulfobutylether-β-cyclodextrin (SB-β-CD).

Aqueous solutions of SB-β-CD at concentrations of 10, 50, 100, 150, 250 and 500 mg/ml were prepared. Excess linezolid was added to each solution. The solutions were stirred for 24 h at 25° C. and were then filtered using 0.2 μm Gelman Acrodisc filter units and assayed for linezolid by HPLC.

Saturation solubility of linezolid in pure water at pH 7 was determined separately to be 2.9±0.1 mg/ml. Saturation solubility of linezolid in aqueous SB-β-CD solutions was determined as shown in Table 1.

TABLE 1

Saturation solubility of linezolid in SB-β-CD solutions

| SB-β-CD concentration (mg/ml) | Solubility of linezolid (mg/ml) |
| --- | --- |
| 10 | 4.3 |
| 50 | 9.5 |
| 100 | 15.9 |
| 150 | 22.1 |
| 250 | 33.4 |
| 500 | 59.9 |

Example 2

A buffered isotonic solution was prepared at pH 4.5, 283 mOsm/kg using a 10 mM citrate buffer solution (0.851 mg/ml citric acid, 1.638 mg/ml sodium citrate) containing 23 mg/ml dextrose and 50 mg/ml SB-β-CD. To 20 ml of this solution was added 100 mg linezolid with heating and stirring until the linezolid was completely dissolved. The resulting solution contained approximately 5 mg/ml linezolid.

Example 3

A buffered isotonic solution was prepared at pH 4.5, 285 mOsm/kg using a 10 mM citrate buffer solution (0.851 mg/ml citric acid, 1.638 mg/ml sodium citrate) containing 100 mg/ml SB-β-CD. To 20 ml of this solution was added 200 mg linezolid with heating and stirring until the linezolid was completely dissolved. The resulting solution contained approximately 10 mg/ml linezolid.

Example 4

A buffered isotonic solution was prepared at pH 4.5, 289 mOsm/kg using a 10 mM citrate buffer solution (0.851 mg/ml citric acid, 1.638 mg/ml sodium citrate) containing 100 mg/ml SB-β-CD. To 100 ml of this solution was added 800 mg linezolid with heating to about 60° C. and stirring until the linezolid was completely dissolved. The resulting solution contained approximately 8 mg/ml linezolid.

The solution was filtered using 0.2 μm Nalgene filterware, and 10 ml of filtered solution was filled into each of ten Kimble-Warsaw Type I glass bottles stoppered with Daikyo 777 stoppers. Eight of the bottles were placed in a 25° C. constant temperature cabinet and two of the bottles were placed in a laboratory refrigerator at 4°-6° C.

No precipitation or color changes were evident after storage for two months under these conditions.

Example 5

Four formulations X, A, B and C suitable for direct intravenous (IV) infusion, and one formulation D suitable for dilution with a standard IV diluent (e.g., saline or 5% dextrose) are prepared, each containing a 600 mg dose of linezolid. Formulation X is included for comparative purposes, containing no cyclodextrin. Compositions of formulation X and formulations A–D are shown in Table 2.

TABLE 2

Compositions of formulations X and A–D (mg/ml)

|  | X | A | B | C | D |
| --- | --- | --- | --- | --- | --- |
| Linezolid | 2 | 8 | 10 | 8 | 60 |
| Sulfobutylether-β-cyclodextrin | — | 100 | 100 | 50 | 500 |
| Sodium citrate dihydrate | 1.638 | 1.638 | 1.638 | 1.638 | 1.638 |
| Citric acid monohydrate granular | 0.851 | 0.851 | 0.851 | 0.851 | 0.851 |
| Dextrose anhydrous granular | * | — | — | 23 | — |
| Water for injection USP | q.s. | q.s. | q.s. | q.s. | q.s. |
| Total volume (ml) containing 600 mg dose | 300 | 75 | 60 | 75 | 10 |

* concentration required to provide isotonic solution in absence of cyclodextrin
q.s. = quantity sufficient to make up to total volume shown The very substantial reduction in volume of IV solution providing a 600 mg dose of linezolid, permitted by addition of SB-β-CD, is clearly seen in Table 2 above.

Example 6

A study was conducted to examine solubility of three oxazolidinone compounds, herein denoted Compound 1, Compound 2 and Compound 3, in an aqueous system containing hydroxypropyl-β-cyclodextrin (HP-β-CD).

Compound 1 is (S)-N-[[3-[3-fluoro-4-(4-(hydroxyacetyl)-1-piperazinyl)phenyl]-2-oxo-5-oxazolidinyl]methyl]acetamide.

Compound 2 is (S)-N-[[3-[3-fluoro-4-(4-morpholinyl)phenyl]-2-oxo-5-oxazolidinyl]methyl]acetamide (linezolid).

Compound 3 is (S)-N-[[3-[3-fluoro-4-(1,1-dioxothiomorpholin-4-yl)phenyl]-2-oxo-5-oxazolidinyl]methyl]acetamide (linezolid).

Aqueous solutions of HP-β-CD at concentrations of 0, 60, 100, 200, 300 and 400 mg/ml were prepared. Compound 1, 2 or 3 in excess amount was added to each solution. The solutions were stirred for 48 h at 37° C. and were then filtered and assayed by HPLC to provide a measure of saturation solubility of Compounds 1, 2 and 3 in each HP-β-CD solution.

The saturation solubilities are shown in graphical form in FIG. 1. Saturation solubility of each oxazolidinone compound was found to be linearly related to HP-β-CD concentration.

What is claimed is:

1. A pharmaceutical composition for administration to a subject having or at risk of infective disease arising from infection by one or more gram-positive bacteria, anaerobic organisms, or acid-fast organisms, the composition comprising an aqueous carrier having in solution therein (a) an oxazolidinone antimicrobial drug concentration that is an effective concentration above the practical limit of solubility of the drug in a substantially isotonic aqueous solution at a physiologically compatible pH, and (b) a pharmaceutically acceptable cyclodextrin compound in a concentration sufficient to maintain the drug in solution at such a drug concentration.

2. The composition of claim 1, wherein the drug concentration is a therapeutically effective amount.

3. The composition of claim 1, wherein the drug concentration is a prophylactically effective amount.

4. The composition of claim 1 that is suitable for parenteral administration.

5. The composition of claim 1 that is suitable for intravenous injection or infusion.

6. The composition of claim 1 wherein the concentration of the drug is about 3 to about 100 mg/ml.

7. The composition of claim 1 wherein the concentration of the drug is about 4 to about 40 mg/ml.

8. The composition of claim 1 wherein the concentration of the drug is about 5 to about 10 mg/ml.

9. The composition of claim 1 wherein the oxazolidinone antimicrobial drug is selected from the group consisting of linezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide, (S)-N-[[3-[5-(4-pyridyl)pyrid-2-yl]-2-oxo-5-oxazolidinyl]methyl]acetamide hydrochloride; and N-[[(5S)-3-[4-(1,1-dioxido-4-thiomorpholinyl)-3,5-difluorophenyl]-2-oxo-5-oxazolidinyl]methyl]acetamide.

10. The composition of claim 1 wherein the oxazolidinone antimicrobial drug is linezolid.

11. The composition of claim 1 wherein the oxazolidinone antimicrobial drug is N-[[(5S)-3-[4-(1,1-dioxido-4-thiomorpholinyl)-3,5-difluorophenyl]-2-oxo-5-oxazolidinyl]methyl]acetamide.

12. The composition of claim 1 wherein the cyclodextrin compound is selected from the group consisting of α-cyclodextrin, β-cyclodextrin, γ-cyclodextrin, alkylcyclodextrins, hydroxyalkylcyclodextrins, carboxyalkylcyclodextrins and sulfoalkylether cyclodextrins.

13. The composition of claim 1 wherein the cyclodextrin compound is selected from hydroxyalkyl-β-cyclodextrins and sulfoalkylether-β-cyclodextrins.

14. The composition of claim 1 wherein the cyclodextrin compound is selected from hydroxypropyl-β-cyclodextrin and sulfobutylether-β-cyclodextrin.

15. The composition of claim 1 wherein the cyclodextrin compound is sulfobutylether-β-cyclodextrin.

16. The composition of claim 1 wherein the cyclodextrin compound is present at a concentration of about 1 to about 500 mg/ml.

17. The composition of claim 1 wherein the cyclodextrin compound is present at a concentration of about 5 to about 200 mg/ml.

18. The composition of claim 1 wherein the cyclodextrin compound is present at a concentration of about 10 to about 100 mg/ml.

19. The composition of claim 1 wherein the cyclodextrin compound is present at a concentration of about 20 to about 50 mg/ml.

20. The composition of claim 1 wherein the cyclodextrin compound is present at a concentration of about 100 to about 500 mg/ml.

21. The composition of claim 1, further comprising a buffering agent and/or an agent for adjusting osmolality in amounts whereby the solution is substantially isotonic and has a physiologically acceptable pH.

22. A method of treating or preventing infective disease in a subject arising from infection by one or more gram-positive bacteria, anaerobic organisms, or acid-fast organisms, the comprising administering to the subject the composition of claim 1 in a therapeutically or prophylactically effective daily dose.

23. The method of claim 22, wherein the composition is diluted in a pharmaceutically acceptable liquid prior to being administered to the subject.

24. The method of claim 22 wherein the subject is a human subject.

25. The method of claim 24 wherein the oxazolidinone antimicrobial drug in the composition is linezolid.

26. The method of claim 25 wherein the daily dose is about 100 to about 1000 mg of linezolid.

27. The method of claim 23 wherein the composition is administered parenterally.

28. The method of claim 23 wherein the composition is administered by intravenous injection or infusion.

29. The method of claim 22 wherein the oxazolidinone antimicrobial drug is N-[[(5S)-3-[4-(1,1-dioxido-4-thiomorpholinyl)-3,5-difluorophenyl]-2-oxo-5-oxazolidinyl]methyl]acetamide.

30. A method of use of a composition of claim 1 in manufacture of a medicament for treating or preventing an infective disease arising from infection by one or more gram-positive bacteria, anaerobic organisms, or acid-fast organisms,

* * * * *